United States Patent
Cronin et al.

(10) Patent No.: US 12,263,157 B2
(45) Date of Patent: Apr. 1, 2025

(54) ALDOSTERONE SYNTHASE INHIBITORS FOR TREATING CHRONIC KIDNEY DISEASE

(71) Applicant: Boehringer Ingelheim International GmbH, Ingelheim am Rhein (DE)

(72) Inventors: Lisa V. Cronin, Grand Island, NY (US); Sibylle Jenny Hauske, Mannheim (DE); Hartmut Ruetten, Ingelheim am Rhein (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 18/079,904

(22) Filed: Dec. 13, 2022

(65) Prior Publication Data

US 2023/0181538 A1 Jun. 15, 2023

Related U.S. Application Data

(60) Provisional application No. 63/289,177, filed on Dec. 14, 2021.

(51) Int. Cl.
*A61K 31/4188* (2006.01)
*A61K 31/4709* (2006.01)
*A61P 13/12* (2006.01)

(52) U.S. Cl.
CPC ...... *A61K 31/4188* (2013.01); *A61K 31/4709* (2013.01); *A61P 13/12* (2018.01)

(58) Field of Classification Search
None
See application file for complete search history.

(56) References Cited

U.S. PATENT DOCUMENTS

| | | | |
|---|---|---|---|
| 5,892,065 A | 4/1999 | Tsukamoto et al. | |
| 7,807,843 B2 | 10/2010 | Goto et al. | |
| 8,293,734 B2 | 10/2012 | Thompson et al. | |
| 9,181,272 B2 | 11/2015 | Balestra et al. | |
| 9,334,285 B2 | 5/2016 | Burke et al. | |
| 9,745,289 B2 | 8/2017 | Hornberger | |
| 2010/0292225 A1 | 11/2010 | Chamoin et al. | |
| 2011/0112067 A1 | 5/2011 | Hartmann et al. | |
| 2011/0118241 A1 | 5/2011 | Hartmann | |
| 2011/0130537 A1 | 6/2011 | Carlberg et al. | |
| 2011/0172217 A1 | 7/2011 | Fujioka et al. | |
| 2013/0143863 A1 | 6/2013 | Aebi et al. | |
| 2014/0206886 A1 | 7/2014 | Scheidt et al. | |
| 2014/0315832 A1 | 10/2014 | Broedl et al. | |
| 2014/0323468 A1 | 10/2014 | Balestra et al. | |
| 2016/0014736 A1 | 1/2016 | Ingelheim | |
| 2016/0024105 A1 | 1/2016 | Burke et al. | |
| 2016/0061161 A1 | 3/2016 | Cowans | |
| 2016/0229807 A1 | 8/2016 | Aebi | |
| 2018/0125813 A1 | 5/2018 | von Eynatten et al. | |
| 2018/0162878 A1 | 6/2018 | Luo et al. | |

FOREIGN PATENT DOCUMENTS

| | | |
|---|---|---|
| CA | 2761859 A1 | 11/2010 |
| CN | 1172806 A | 2/1998 |
| CN | 1692103 A | 11/2005 |
| CN | 102741259 A | 10/2012 |
| CN | 109053637 A | 12/2018 |
| EP | 0666256 A1 | 8/1995 |
| EP | 2341052 A1 | 7/2011 |
| JP | 2007297305 A | 11/2007 |
| JP | 2011530621 A | 12/2011 |
| JP | 2012526774 A | 11/2012 |
| WO | 0198273 A1 | 12/2001 |
| WO | 2007100295 A1 | 9/2007 |
| WO | 2007116099 A1 | 10/2007 |
| WO | 2007117982 A2 | 10/2007 |
| WO | 2008027284 | 4/2008 |
| WO | 2009135651 | 11/2009 |
| WO | 2009135651 A1 | 11/2009 |
| WO | 2010042477 A1 | 4/2010 |
| WO | 2014055595 | 4/2010 |
| WO | 2010107765 A1 | 9/2010 |
| WO | 2010129467 | 11/2010 |

(Continued)

OTHER PUBLICATIONS

Bolignano et al., Cochrane Database Syst Rev. Apr. 29, 2014;(4):CD007004. (Year: 2014).*
Ménard et al., J Transl Med. Dec. 10, 2014;12:34 (Year: 2014).*
Yang et al., Current Opinion in Pharmacology, vol. 27, 2016, p. 78-85 (Year: 2016).*
Frimodt-Møller M, Persson F, Rossing P. Mitigating risk of aldosterone in diabetic kidney disease. Curr Opin Nephrol Hypertens. Jan. 2020;29(1):145-151. doi: 10.1097/MNH.0000000000000557. PMID: 31599747; PMCID: PMC6903382 (Year: 2020).*
Frampton, J.E. Drugs 78, 1037-1048 (2018) (Year: 2018).*
Herrington, the potential for improving cardio-renal outcomes by sodium-glucose co-transporter-2 inhibition in people with chronic kidney disease, Clin. Kidney Journal, 2018, 13 pages.
Kdigo, 2020 clinical practice guideline for diabetes managment in chronic kidney disease, Kidney Int. supplement, vol. 98, 2020, p. S1-S115.
Birge, Pharmaeutical Salts, J. Pharm. Sci, vol. 66, 1977, p. 1-19.

(Continued)

*Primary Examiner* — Jeffrey S Lundgren
*Assistant Examiner* — Anthony Joseph Seitz
(74) *Attorney, Agent, or Firm* — David L. Kershner

(57) ABSTRACT

The present invention relates to treatment of chronic kidney disease by administering to patients in need thereof a compound of formula (1):

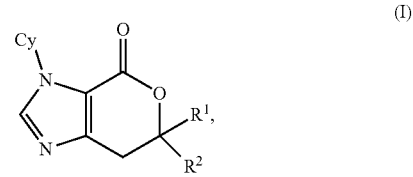

and pharmaceutically acceptable salts thereof, wherein Cy, $R^1$ and $R^2$ are as defined herein. The invention further relates to the use of the compounds of formula (1) in combination with sodium-glucose cotransporter-2 (SGLT2) inhibitors.

15 Claims, No Drawings

(56) References Cited

FOREIGN PATENT DOCUMENTS

| WO | 2013037779 | | 3/2013 | |
| WO | 2013041591 | | 3/2013 | |
| WO | 2013156423 | | 10/2013 | |
| WO | 2014055595 | A1 | 4/2014 | |
| WO | 2014130608 | A1 | 8/2014 | |
| WO | 2014179186 | A1 | 11/2014 | |
| WO | 2015101958 | A2 | 7/2015 | |
| WO | WO-2016014736 | A1 * | 1/2016 | ......... A61K 31/4188 |
| WO | 2016144844 | A1 | 9/2016 | |

OTHER PUBLICATIONS

Kdigo, Clinical Practice guifeline for acute kidney injury, Kidney Int. Supplement, vol. 2, 2012, p. 1-138.
Jardine, Renal, cardiovascular and Safety outcomes of canagliflozin by baseline kidney function, J. of amer. nephrological society, vol. 31, 2020, p. 1128-1139.
Farxiga, DAPA-CKD Phase III trial reduced worsening of kidney function, risk of cardiovacular or renal death in patients with chronic kidney disease, AstraZeneca Press Release, Oct. 23, 2020.
Tuttle, Efficacy and safety of aldosterone synthase inhibition with and without empagliflozin for chornoic kidney disease, Lancet, Published online Dec. 15, 2023, https://doi.org/10.1016/S0140-6736(23)02408-x,).
International Search Report, PCT/ISA/210, mailed Aug. 8, 2014, for PCT/US2014/035596.
International Search Report, Mailed Feb. 16, 2016, PCT/ISA220, for PCT/US2015055421.
Lucas, J. Med. Chem., vol. 51, "In Vivo Active aldosterone synthase inhibitors with improved selectivity: Lead optimization providing a series of Pyridine substituted 3,4 Dihydro-1H quinolin-2-one derivatives", 2008.
Anderson, Aldosterone Synthase Inhibition in Hypertenstion, Curr. Hypertens Rep., 2013, 15, p. 484-488.
Hu, Aldosterone Synthase Inhibitors as Promising Treatments for Mineralocorticoid Dependent Cardiovascualr and renal Diseases, J. Med Chem, 2014, 57, p. 5011-5022.
Banki, Aldosterone Antagonists in Monotherapy are Protective against Streptozotocin-Induced Diabetic Nephropathy in Rats, PLOS plus One, 2012, 7, e39938.
Dorrance, Interfering with mineralcortocid receptor activation: the past, present and future, Prime Reports, 2014, p. 6-61.
Hargovan, Aldoesterone Synthase Inhibitors in hypertension: current status and future possibilities, Journal of the Royal Society of Medicine, 2014, 0, p. 1-9.
Heim, Overcominh undesirable CYP1A2 Inhibition of Pyridylnaphthaline-Type Aldoesterone Synthase Inhibtiors: Influence of Heteroaryl Derivatization on Potency and Selectivity Journal of Medicinal Chem, 2008, 501, p. 5011-5022.
Azzizi, Nephrol Dial Transplant 2013, 28, p. 36-43.
International Report on Patetability for PCT/US2017038440 mailed Jan. 10, 2019.
Sonegawa, Regioselective Alkylation of 2-Alkyl-5.6.7.8-tetrahydro-3H-cycloheptimidazol-4ones and 2-Alkyl-3H-cycloheptimidazol-4-ones, Chem and pharm Bulletin, 2006, vol. 54, p. 706-710.
Mityanov, Regioselective synthesis of 2-unsubstituted 1-aryl-4-and 1-aryl-5 acylimiazoles" Tetrahedron, 2014, vol. 70, p. 3545-3552.
Bornstein, Phase 1C study of the aldosterone synthase inhibitor BI 690517 in diabetic patients with kidney disease, Journal of the American Society of Nephrology, vol. 32, 2021, p. 264-265.

International Search Report for PCTUS2020030337 mailed Aug. 10, 2020.
Abstract for JP2007297305 cited herein.
International Search Report and Written Opinion, PCT, US 2015/041648, PCT/ISA/220, mailed Oct. 26, 2015.
Hartmann, et al., "Discovery of selective CYP11B2 (aldosterone synthase) inhibitors for the therapy of congestive heart failure and myocardial fibrosis", Euro. Journal of Medicinal Chamistry, vol. 38, No. 4, 2003.
International Search Report and Written Opinion, Form ISA220, mailed Feb. 22, 2016, for PCT/US2015063064.
International Preliminary Report on Patentability, Form PCT.IB/373, mailed Jun. 6, 2017.
Martin, Synthesis of annulated pyridines as inhibitors of aldosterone synthase, Organic Biomol. Chemistry, vol. 14, 2016, 2016.
Azizi, Aldosterone synthase inhibitors in humans, Nephrol Dial Translplant, vol. 28, p. 36-43. 2012.
Hu, Aldosterone Synthase Inhibitors as promising treatments for mineralocorticoid dependent cardiovascular and renal diseases, Phamraceutical and Medicinal chem, vol. 57, 2014, p. 5011-5022.
Banki, Aldosterone Antagonists in Monotherapy are protective against Streptozotocin-induced diabetic Neuropathy in rats, PLOS One, vol. 7, e39938, 2012.
Andersen, Aldosterone Synthase Inhibitors in Hypertension, Current Hypertens Rep., vol. 15, 2013, p. 484-488.
Hargovan, Aldosterone synthase inhibitors in hypertension: current status and future possibilities, Journal of the Royal Society of Medicine Cardiovascular Disease, 2014, p. 1-9.
Dorrance, Interfering with mineralcorticoid receptor activation: the past, present and future, F1000 Prime Reports, 2014, p. 6-61.
Shen, Synthesis of 2-(phenoxymehyl)oxirane derivatives through unexpected rearrangment of oxiran-2-ylmethyl benzenesulfomates, Synthetic Cimmuications, vol. 47, 2017, 6 pages.
Evans, A narrative review of chronic kidney disease inclinical practice, Adv. Ther., vol. 9, 2022, 11 pages.
Gilligan, Hyperkalemia and Hypokalemia in CKD, ACKD, vol. 24, 2017, p. 315-318.
Neuen, Sodium-Glucose Cotransporter 2 inhibitors and Risk of Hyperkalemia in People with type 2 diabetes, Circulation, vol. 10, 2011, 11 pages.
Verma, Aldosterone in chronic kidney disease and renal outcomes, ESC, vol. 43, 2022, 11 pages.
Xiao, Phenylsulfone directed diastereoselective cyclization of an epoxy aalysilane system, J. of Organic Chem., vol. 53, 1988, p. 4869-4872.
Mikleusevic, Oxazolidinone Synthesis through Halohydrin Dehalogenese Catalyzed dynamic kinetic resolution, Advanced Synthesis and Catalysis, vol. 357, 2015, p. 1709-171.
Mende, Chronic Kidney Disease, and SGLT2 Inhibitors, Adv. Thera, vol. 10, 2022, p. 148-164.
Wanner, Empa and Progression of Kidney Disease in Type 2 diabetes, The N. England J of Med., vol. 39, 2022, p. 148-164.
International Search Report and Written Opinion for PCT/US2022/052631, mailed Mar. 23, 2023.
Frimodt-Moller, Mitigating Risk of Aldosterone in Diabetic Kidney Disease, Current Opinion, vol. 29, 2020, 7 pages.
Klunder, Arenesulfonate Derivatives of Homochiral Glycidol, J. Org. Chem, vol. 54, 1989, p. 1254-1304.
Mitsuhiko, Gas and liquid purification technology, Electrochemistry, vol. 33, 1965, p. 458-462.

* cited by examiner

ALDOSTERONE SYNTHASE INHIBITORS FOR TREATING CHRONIC KIDNEY DISEASE

FIELD OF THE INVENTION

The invention relates to the use of certain aldosterone synthase inhibitors for treating certain disorders including diabetic and non-diabetic chronic kidney disease. The invention further relates to the use of the aldosterone synthase inhibitors in combination with sodium-glucose cotransporter-2 (SGLT2) inhibitors.

BACKGROUND

Chronic Kidney Disease (CKD) is the leading cause of kidney damage and end-stage renal disease (ESRD). The 5-year survival rate of dialysis patients is 35%, which decreases to only 25% in diabetic dialysis patients. As a result, CKD puts a large burden on healthcare systems worldwide, e.g. in the U.S. costs per patient exceed $75,000 annually. In addition to direct renal consequences, reduced kidney function is also a major trigger for cardio-vascular events. Overall, around 12% of the general population in Europe have CKD stages 3 to 5, with considerable variation across countries, ranging from 4.1% to 25.5%.

Diabetes is the main cause of CKD in most countries, accounting for 40% or more of new cases. As glomerular filtration rate (GFR) declines, there is a linear increase in mortality, with 2- to 5-fold increases in patients with GFR <45 mL/min/1.73 m² compared with patients with GFR >60 mL/min/1.73 m². Declining renal function is associated with an increasing risk for coronary heart disease, stroke, and heart failure. Diabetic nephropathy is the leading cause of kidney damage and end-stage renal disease (ESRD), accounting for >40% of patients on dialysis. For patients on dialysis, the 5-year survival rate is 35%; for patients with diabetes who are on dialysis, the 5-year survival rate is only 25%.

At present, only a limited number of therapeutic options are available to delay renal decline in patients with CKD. Angiotensin-converting enzyme (ACE) inhibitors (ACEis) and angiotensin receptor blockers (ARBs) can reduce albuminuria and slow the rate of progression in proteinuric nephropathies. However, in clinical trials in patients with diabetic nephropathy, the relative risk reduction for the composite primary endpoint of all-cause death, ESRD and doubling of serum creatinine in trials was only moderate (16% in the RENAAL trial and 19% in the IDNT trial). Recently, the sodium glucose cotransporter 2 (SGLT2) inhibitor empagliflozin has been shown to reduce the risk of kidney disease progression in people with type 2 diabetes. An exploratory analysis of the EMPA-REG OUTCOME trial indicated that empagliflozin reduced the incidence of the composite outcome of doubling of creatinine, the need to start kidney replacement therapy, or renal death by 46% (HR 0.54, 95% CI 0.40-0.75). These benefits were similar regardless of baseline ACEi or ARB use and there was no evidence of an increased risk of hyperkalaemia or acute kidney injury. (See Wanner C, et al, EMPA-REG OUTCOME Investigators; Empagliflozin and progression of kidney disease in type 2 diabetes. New England Journal of Medicine, published Jun. 14, 2016, p. 323-334.) In the EMPEROR-Reduced trial, which was conducted in patients with heart failure with reduced ejection fraction, empagliflozin reduced the risk of the exploratory composite renal endpoint (chronic dialysis, kidney transplant, or sustained reduction in eGFR) by 50% in the overall trial population. This and was also consistent en in patients with and without CKD at baseline. Cardio-Kidney benefits of empagliflozin are currently being investigated in patients with CKD and high risk for progression in the ongoing EMPA-KIDNEY study. (See Herrington W G, et al., The potential for improving cardio-renal outcomes by sodium-glucose co-transporter-2 inhibition in people with chronic kidney disease: a rationale for the EMPA-KIDNEY study. Clinical Kidney Journal, Published: 25 Oct. 2018.)

Increasing evidence is indicating that SGLT2 inhibitors are likely to become a new treatment option for patients across a broad range of CKD phenotypes. The SGLT2 inhibitor canagliflozin has received FDA approval for the treatment of patients with diabetic kidney disease. In the CREDENCE trial, canagliflozin provided a relative risk reduction of 30% for the composite endpoint of doubling of serum creatinine, ESRD or renal/CV death on top of standard of care. A large-scale clinical outcome trial (DAPA-CKD) evaluating the SGLT2 inhibitor dapagliflozin in patients with CKD (with or without type 2 diabetes) was stopped early due to overwhelming efficacy. Data reported in August 2020 showed that dapagliflozin resulted in 39% relative risk reduction (RRR) for the composite primary endpoint (≥50% eGFR decline/ESKD/renal or CV death). Dapagliflozin also resulted in 39% RRR for composite secondary endpoint of CV death and HF hospitalization and 31% RRR for all-cause mortality.

Current guidelines have started to incorporate this new evidence by recommending SGLT2 inhibitors with proven benefits as an integral part of the treatment regimen for patients with type 2 diabetes and CKD or CV risk. (See de Boer I H, Caramori L, Chan J C N, et al. KDIGO 2020 clinical practice guideline for diabetes management in chronic kidney disease. Kidney Int Suppl 2020. 98: S1-S115.) Recommendations for nondiabetic kidney disease are likely to follow soon in the light of the new and upcoming evidence. Despite this advance, the residual renal and cardiovascular risks for patients remain unacceptably high for patients with CKD, warranting continued efforts to provide new treatments, particularly for fast-progressing patients (with GFR reductions >3 ml/min/1.73 m²/year) that are at considerably increased risk.

Empagliflozin is an orally available SGLT2 inhibitor, which is indicated for reduction of blood glucose in patients with Type 2 Diabetes Mellitus (T2DM), and for risk reduction of cardiovascular (CV) death in patients with T2DM and established CV disease. Recently, empagliflozin has been shown to reduce the risk of kidney disease progression in people with type 2 diabetes. An exploratory analysis of the EMPAREG OUTCOME trial indicated that empagliflozin reduced the incidence of the composite outcome of doubling of creatinine, the need to start kidney replacement therapy, or renal death by 46% (HR 0.54, 95% CI 0.40-0.75). These benefits were similar regardless of baseline ACEi or ARB use and there was no evidence of an increased risk of hyperkalaemia or acute kidney injury. Empagliflozin is currently being investigated for the treatment of CKD in the ongoing EMPA-KIDNEY renal outcome trial.

Despite significant improvements of clinical outcomes with SGLT2 inhibitor treatment, there is a high residual risk for patients with CKD to further progress. Particularly those with continued fast progression have an excessive risk for poor clinical outcomes and have a high unmet need for further treatment options which are safe and efficacious when added on top of standard of care (i.e. RAAS inhibitor and SGLT2 inhibitor). Particularly, those with continued fast progression, have an excessive risk for poor clinical outcomes and have a high unmet need for further treatment options which are safe and efficacious when added on top of standard of care (i.e. RAASi and SGLT2i).

BRIEF SUMMARY OF THE INVENTION

There is a need for new treatments for CKD patients who are at high risk for disease progression especially patients with fast progression (e.g. eGFR decline of >3 ml/min/year), The present invention relates to methods for treating CKD comprising administering a therapeutically effective amount of an aldosterone synthase inhibitor ("AS inhibitor") to a patient in need thereof, optionally in combination with an SLGT2 inhibitor ("the methods of the invention").

WO2016/014736 and WO2016/061161 describe oral, small-molecule inhibitors of human aldosterone synthase. Inhibition/blockage of aldosterone is reportedly useful for reducing kidney fibrosis and improvement of glomerular filtration rate and albuminuria in models of chronic kidney disease (CKD) and diabetic nephropathy.

In one embodiment of the invention, the AS inhibitor used in the methods of the invention is a compound of formula (I)

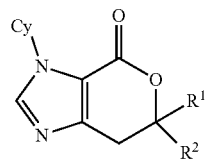

(I)

wherein:
Cy is a monocyclic or bicyclic ring system selected from $C_{3-10}$cycloalkyl, heterocyclyl, aryl and heteroaryl,
  wherein each of the said $C_{3-10}$cycloalkyl, heterocyclyl, aryl and heteroaryl groups is optionally and independently substituted with one, two, or three substituent groups selected from halogen, —$C_{1-3}$-alkyl, —$OC_{1-3}$-alkyl, —$CF_3$, cyano, oxo, —$N(C_{1-3}$-alkyl)$_2$, —$NH(C_{1-3}$-alkyl), —$NHCOC_{1-3}$-alkyl, —$C(O)C_{1-3}$-alkyl, —$C(O)OC_{1-3}$alkyl, hydroxy-$C_{1-3}$alkyl, or heteroaryl;
$R^1$ and $R^2$ are independently selected from H, $C_{1-3}$alkyl, hydroxy$C_{1-3}$alkyl, —$CH_2NHC(O)OC_{1-4}$alkyl, —$CH_2OC(O)C_{1-4}$alkyl, —$C(O)OC_{1-4}$-alkyl, —$C(O)H$, —$COOH$, —$C(O)NHC_{1-4}$-alkyl and $C(O)N(C_{1-4}$-alkyl)$_2$, or
$R^1$ and $R^2$ taken together form a $C_{3-6}$cycloalkyl or $C_{3-6}$-heterocyclyl;
or a salt thereof.

Unless otherwise stated, the terms "compound of formula (I)" and "the AS inhibitor of the invention" are used interchangeably.

In another embodiment, the methods of the invention relate to the use of the compounds of formula (I) as described according to the embodiment above and wherein
Cy is a phenyl, cyclohexyl, indanyl, 2,3-dihydrobenzofuranyl or tetrahydroquinolinyl group, each optionally substituted with one, two, or three substituent groups independently selected from —Cl, —F, $C_{1-3}$alkyl, oxo and CN; and
$R^1$ and $R^2$ are independently selected from H, $C_{1-3}$alkyl, hydroxy$C_{1-3}$alkyl, —$CH_2NHC(O)OC_{1-4}$alkyl, —$C(O)N(C_{1-4}$-alkyl)$_2$ and —$CH_2OC(O)C_{1-4}$alkyl.

In another embodiment, the methods of the invention relate to the use of the compounds of formula (I) according to any of the embodiments above and wherein
Cy is phenyl optionally substituted with one, two, or three substituent groups independently selected from —Cl, —F, $C_{1-3}$alkyl and CN.

In another embodiment, the methods of the invention relate to the use of the compounds of formula (I) as described according to any of the embodiments above and wherein Cy is phenyl substituted with one, two, or three substituent groups independently selected from —Cl, —F, $C_{1-3}$alkyl and CN.

In another embodiment, the methods of the invention relate to the use of the compounds of formula (I) as described according to any of the embodiments above and wherein Cy is phenyl substituted with CN and optionally substituted with one or two, additional groups independently selected from —Cl, —F and $C_{1-3}$alkyl.

In another embodiment, the methods of the invention relate to the use of the compounds of formula (I) as described according to any of the embodiments above and wherein
$R^1$ is —$CH_3$; and
$R^2$ is —$CH_3$ or —$CH_2OH$.

In another embodiment, the methods of the invention relate to the use of the compounds of formula (I) as described according to any of the embodiments above and wherein
$R^1$ is —$CH_3$; and
$R^2$ is —$CH_2OH$.

In another embodiment, the methods of the invention relate to the use of the compounds of formula (I) as described according to any of the embodiments above and wherein
$R^1$ is —$CH_3$; and
$R^2$ is —$CH_3$.

Table 1 shows representative compounds of the invention which can used according to the methods of the invention.

TABLE 1

| Compound | Structure | Name |
|---|---|---|
| 1 | 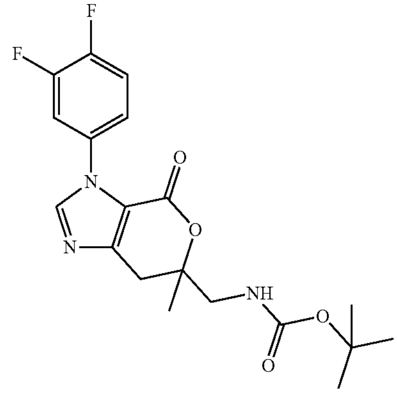 [SMILES: CC(C)(C)OC(=O)NCC1(C)Cc2ncn(-c3ccc(F)c(F)c3)c2C(=O)O1] | tert-butyl N-{[3-(3,4-difluorophenyl)-6-methyl-4-oxo-3H,4H,6H,7H-pyrano[3,4-d]imidazol-6-yl]methyl} carbamate |

TABLE 1-continued

| Compound | Structure | Name |
|---|---|---|
| 2 | 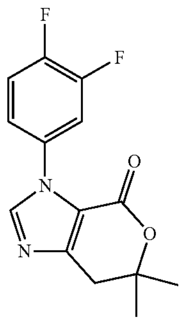 [SMILES: CC1(C)Cc2ncn(-c3ccc(F)c(F)c3)c2C(=O)O1] | 3-(3,4-difluorophenyl)-6,6-dimethyl-3H,4H,6H,7H-pyrano[3,4-d]imidazol-4-one |
| 3 | 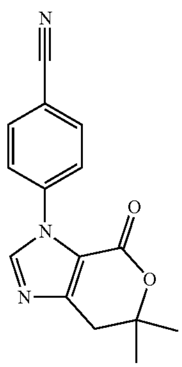 [SMILES: CC1(C)Cc2ncn(-c3ccc(C#N)cc3)c2C(=O)O1] | 4-{6,6-dimethyl-4-oxo-3H,4H,6H,7H-pyrano[3,4-d]imidazol-3-yl}benzonitrile |
| 4 | 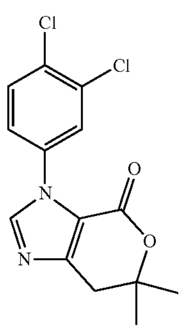 [SMILES: CC1(C)Cc2ncn(-c3ccc(Cl)c(Cl)c3)c2C(=O)O1] | 3-(3,4-dichlorophenyl)-6,6-dimethyl-3H,4H,6H,7H-pyrano[3,4-d]imidazol-4-one |
| 5 | 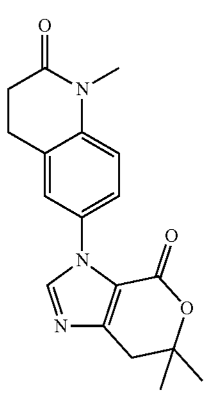 [SMILES: CN1C(=O)CCc2cc(-n3cnc4c3C(=O)OC(C)(C)C4)ccc21] | 6-{6,6-dimethyl-4-oxo-3H,4H,6H,7H-pyrano[3,4-d]imidazol-3-yl}-1-methyl-1,2,3,4-tetrahydroquinolin-2-one |

TABLE 1-continued

| Compound | Structure | Name |
|---|---|---|
| 6 | 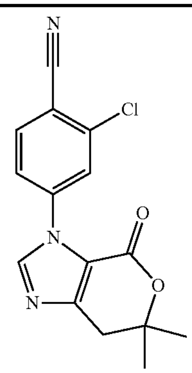 | 2-chloro-4-{6,6-dimethyl-4-oxo-3H,4H,6H,7H-pyrano[3,4-d]imidazol-3-yl}benzonitrile |
| 7 | 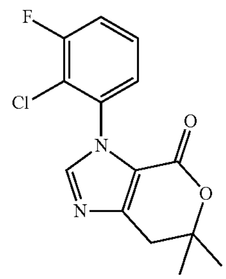 [SMILES: CC1(C)Cc2ncn(-c3cccc(F)c3Cl)c2C(=O)O1] | 3-(2-chloro-3-fluorophenyl)-6,6-dimethyl-3H,4H,6H,7H-pyrano[3,4-d]imidazol-4-one |
| 8 | 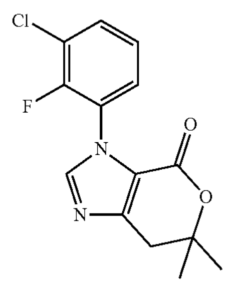 [SMILES: CC1(C)Cc2ncn(-c3cccc(Cl)c3F)c2C(=O)O1] | 3-(3-chloro-2-fluorophenyl)-6,6-dimethyl-3H,4H,6H,7H-pyrano[3,4-d]imidazol-4-one |
| 9 | 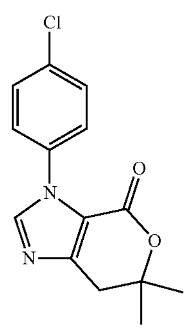 [SMILES: CC1(C)Cc2ncn(-c3ccc(Cl)cc3)c2C(=O)O1] | 3-(4-chlorophenyl)-6,6-dimethyl-3H,4H,6H,7H-pyrano[3,4-d]imidazol-4-one |
| 10 | 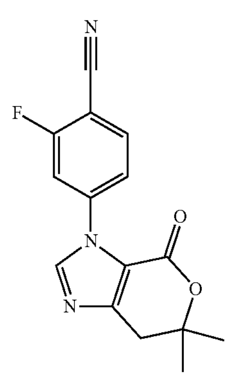 [SMILES: CC1(C)Cc2ncn(-c3ccc(C#N)c(F)c3)c2C(=O)O1] | 4-{6,6-dimethyl-4-oxo-3H,4H,6H,7H-pyrano[3,4-d]imidazol-3-yl}-2-fluorobenzonitrile |

TABLE 1-continued

| Compound | Structure | Name |
|---|---|---|
| 11 | 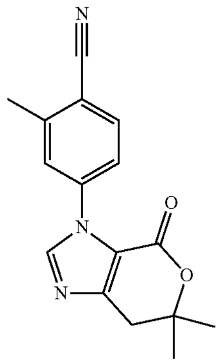 | 4-{6,6-dimethyl-4-oxo-3H,4H,6H,7H-pyrano[3,4-d]imidazol-3-yl}-2-methylbenzonitrile |
| 12 | 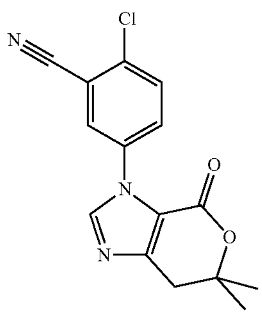 [SMILES: CC1(C)Cc2ncn(-c3ccc(Cl)c(C#N)c3)c2C(=O)O1] | 2-chloro-5-{6,6-dimethyl-4-oxo-3H,4H,6H,7H-pyrano[3,4-d]imidazol-3-yl}benzonitrile |
| 13 | 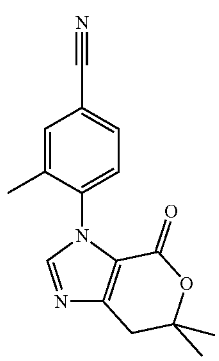 | 4-{6,6-dimethyl-4-oxo-3H,4H,6H,7H-pyrano[3,4-d]imidazol-3-yl}-3-methylbenzonitrile |
| 14 | 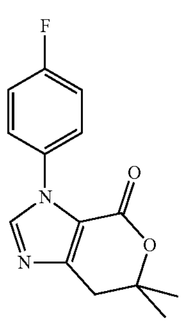 [SMILES: CC1(C)Cc2ncn(-c3ccc(F)cc3)c2C(=O)O1] | 3-(4-fluorophenyl)-6,6-dimethyl-3H,4H,6H,7H-pyrano[3,4-d]imidazol-4-one |

TABLE 1-continued

| Compound | Structure | Name |
|---|---|---|
| 15 | 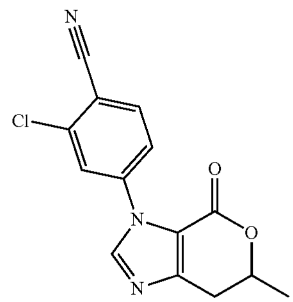 [SMILES: CC1Cc2ncn(-c3ccc(C#N)c(Cl)c3)c2C(=O)O1] | 2-chloro-4-[6-methyl-4-oxo-3H,4H,6H,7H-pyrano[3,4-d]imidazol-3-yl]benzonitrile |
| 16 | 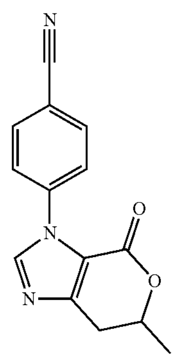 [SMILES: CC1Cc2ncn(-c3ccc(C#N)cc3)c2C(=O)O1] | 4-[6-methyl-4-oxo-3H,4H,6H,7H-pyrano[3,4-d]imidazol-3-yl]benzonitrile |
| 17 | 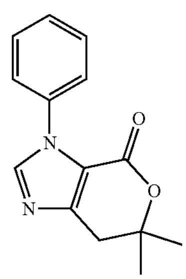 [SMILES: CC1(C)Cc2ncn(-c3ccccc3)c2C(=O)O1] | 6,6-dimethyl-3-phenyl-3H,4H,6H,7H-pyrano[3,4-d]imidazol-4-one |
| 18 | 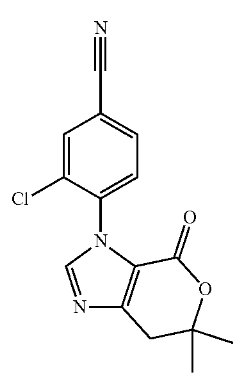 [SMILES: CC1(C)Cc2ncn(-c3ccc(C#N)cc3Cl)c2C(=O)O1] | 3-chloro-4-{6,6-dimethyl-4-oxo-3H,4H,6H,7H-pyrano[3,4-d]imidazol-3-yl}benzonitrile |

TABLE 1-continued

| Compound | Structure | Name |
|---|---|---|
| 19 | 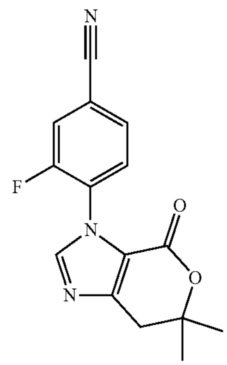 [SMILES: CC1(C)Cc2ncn(-c3ccc(C#N)cc3F)c2C(=O)O1] | 4-{6,6-dimethyl-4-oxo-3H,4H,6H,7H-pyrano[3,4-d]imidazol-3-yl}-3-fluorobenzonitrile |
| 20 | 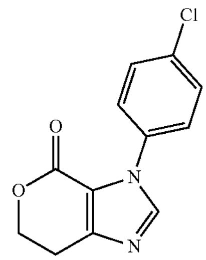 [SMILES: O=C1OCCc2ncn(-c3ccc(Cl)cc3)c21] | 3-(4-chlorophenyl)-3H,4H,6H,7H-pyrano[3,4-d]imidazol-4-one |
| 21 | 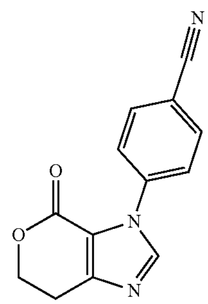 [SMILES: N#Cc1ccc(-n2cnc3c2C(=O)OCC3)cc1] | 4-{4-oxo-3H,4H,6H,7H-pyrano[3,4-d]imidazol-3-yl}benzonitrile |
| 22 | 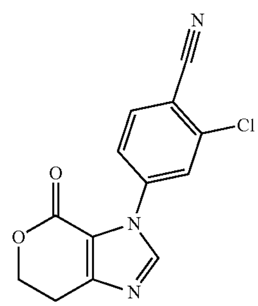 [SMILES: N#Cc1ccc(-n2cnc3c2C(=O)OCC3)cc1Cl] | 2-chloro-4-{4-oxo-3H,4H,6H,7H-pyrano[3,4-d]imidazol-3-yl}benzonitrile |
| 23 | 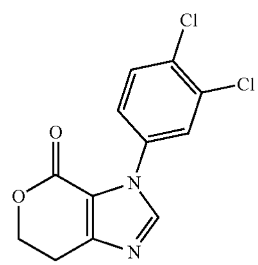 [SMILES: O=C1OCCc2ncn(-c3ccc(Cl)c(Cl)c3)c21] | 3-(3,4-dichlorophenyl)-3H,4H,6H,7H-pyrano[3,4-d]imidazol-4-one |

TABLE 1-continued

| Compound | Structure | Name |
|---|---|---|
| 24 | 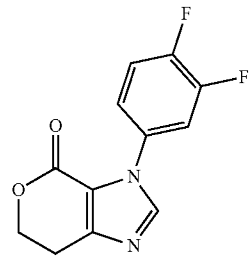 [SMILES: O=C1OCCc2ncn(-c3ccc(F)c(F)c3)c21] | 3-(3,4-difluorophenyl)-3H,4H,6H,7H-pyrano[3,4-d]imidazol-4-one |
| 25 | 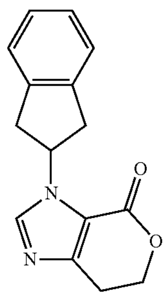 [SMILES: O=C1OCCc2ncn(C3Cc4ccccc4C3)c21] | 3-(2,3-dihydro-1H-inden-2-yl)-3H,4H,6H,7H-pyrano[3,4-d]imidazol-4-one |
| 26 | 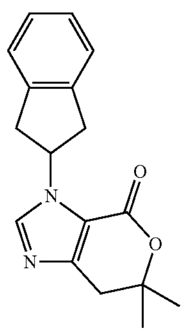 [SMILES: CC1(C)Cc2ncn(C3Cc4ccccc4C3)c2C(=O)O1] | 3-(2,3-dihydro-1H-inden-2-yl)-6,6-dimethyl-3H,4H,6H,7H-pyrano[3,4-d]imidazol-4-one |
| 27 | 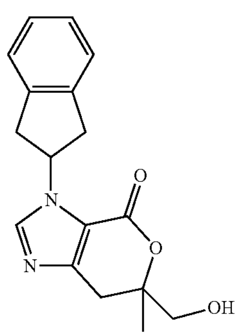 [SMILES: CC1(CO)Cc2ncn(C3Cc4ccccc4C3)c2C(=O)O1] | 3-(2,3-dihydro-1H-inden-2-yl)-6-(hydroxymethyl)-6-methyl-3H,4H,6H,7H-pyrano[3,4-d]imidazol-4-one |
| 28 | 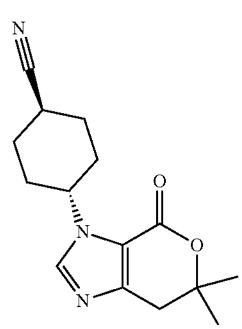 [SMILES: CC1(C)Cc2ncn([C@H]3CC[C@H](C#N)CC3)c2C(=O)O1] | trans-4-(6,6-Dimethyl-4-oxo-6,7-dihydro-4H-pyrano[3,4-d]imidazol-3-yl)-cyclohexanecarbonitrile |

TABLE 1-continued

| Compound | Structure | Name |
|---|---|---|
| 29 A | 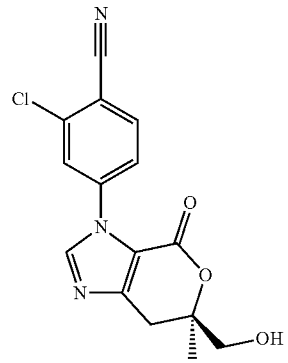 [SMILES: C[C@]1(CO)Cc2ncn(-c3ccc(C#N)c(Cl)c3)c2C(=O)O1] | 2-chloro-4-[(6R)-6-(hydroxymethyl)-6-methyl-4-oxo-3H,4H,6H,7H-pyrano[3,4-d]imidazol-3-yl]benzonitrile |
| 29 B | 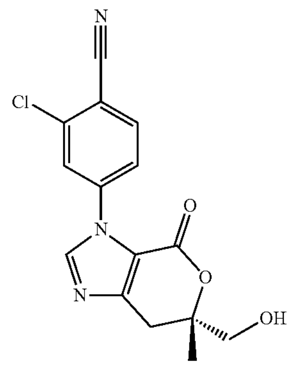 [SMILES: C[C@@]1(CO)Cc2ncn(-c3ccc(C#N)c(Cl)c3)c2C(=O)O1] | 2-chloro-4-[(6S)-6-(hydroxymethyl)-6-methyl-4-oxo-3H,4H,6H,7H-pyrano[3,4-d]imidazol-3-yl]benzonitrile |
| 30 | 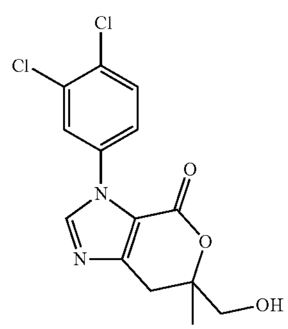 [SMILES: CC1(CO)Cc2ncn(-c3ccc(Cl)c(Cl)c3)c2C(=O)O1] | 3-(3,4-dichlorophenyl)-6-(hydroxymethyl)-6-methyl-3H,4H,6H,7H-pyrano[3,4-d]imidazol-4-one |
| 31 | 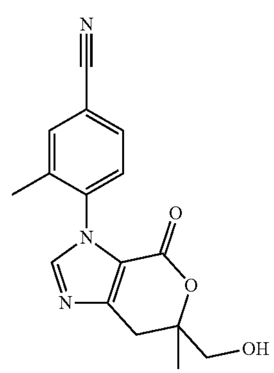 [SMILES: Cc1cc(C#N)ccc1-n1cnc2c1C(=O)OC(C)(CO)C2] | 4-[6-(hydroxymethyl)-6-methyl-4-oxo-3H,4H,6H,7H-pyrano[3,4-d]imidazol-3-yl]-3-methylbenzonitrile |

TABLE 1-continued

| Compound | Structure | Name |
|---|---|---|
| 32 | 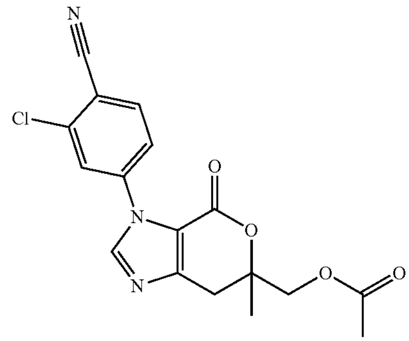 [SMILES: CC(=O)OCC1(C)Cc2ncn(-c3ccc(C#N)c(Cl)c3)c2C(=O)O1] | [3-(3-chloro-4-cyanophenyl)-6-methyl-4-oxo-3H,4H,6H,7H-pyrano[3,4-d]imidazol-6-yl]methyl acetate |
| 33 | 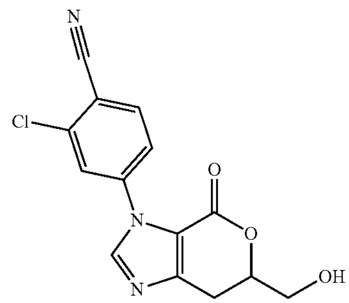 [SMILES: N#Cc1ccc(-n2cnc3c2C(=O)OC(CO)C3)cc1Cl] | 2-chloro-4-[6-(hydroxymethyl)-4-oxo-3H,4H,6H,7H-pyrano[3,4-d]imidazol-3-yl]benzonitrile |
| 34 | 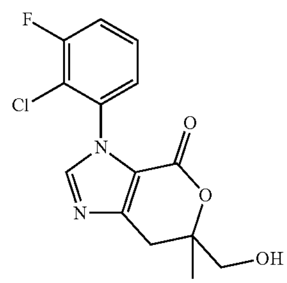 [SMILES: CC1(CO)Cc2ncn(-c3cccc(F)c3Cl)c2C(=O)O1] | 3-(2-chloro-3-fluorophenyl)-6-(hydroxymethyl)-6-methyl-3H,4H,6H,7H-pyrano[3,4-d]imidazol-4-one |
| 35 | 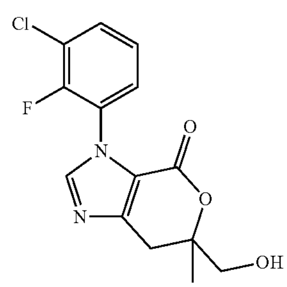 [SMILES: CC1(CO)Cc2ncn(-c3cccc(Cl)c3F)c2C(=O)O1] | 3-(3-chloro-2-fluorophenyl)-6-(hydroxymethyl)-6-methyl-3H,4H,6H,7H-pyrano[3,4-d]imidazol-4-one |
| 36 | 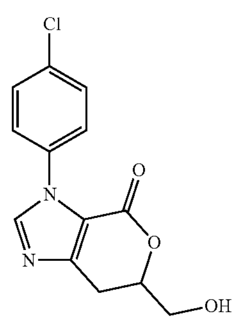 [SMILES: O=C1OC(CO)Cc2ncn(-c3ccc(Cl)cc3)c21] | 3-(4-chlorophenyl)-6-(hydroxymethyl)-3H,4H,6H,7H-pyrano[3,4-d]imidazol-4-one |

TABLE 1-continued

| Compound | Structure | Name |
|---|---|---|
| 37 | 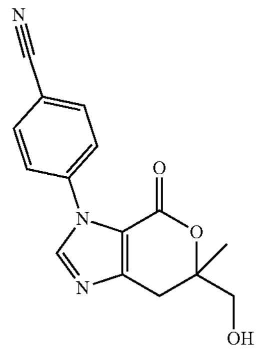 [SMILES: CC1(CO)Cc2ncn(-c3ccc(C#N)cc3)c2C(=O)O1] | 4-[6-(hydroxymethyl)-6-methyl-4-oxo-3H,4H,6H,7H-pyrano[3,4-d]imidazol-3-yl]benzonitrile |
| 38 | 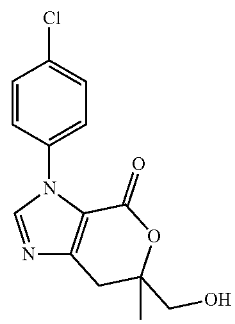 [SMILES: CC1(CO)Cc2ncn(-c3ccc(Cl)cc3)c2C(=O)O1] | 3-(4-chlorophenyl)-6-(hydroxymethyl)-6-methyl-3H,4H,6H,7H-pyrano[3,4-d]imidazol-4-one |
| 39 | 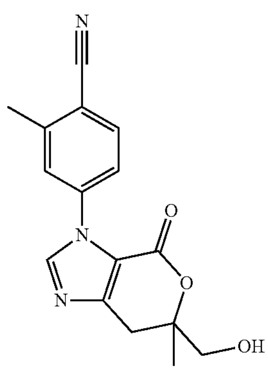 [SMILES: Cc1cc(-n2cnc3c2C(=O)OC(C)(CO)C3)ccc1C#N] | 4-[6-(hydroxymethyl)-6-methyl-4-oxo-3H,4H,6H,7H-pyrano[3,4-d]imidazol-3-yl]-2-methylbenzonitrile |
| 40 | 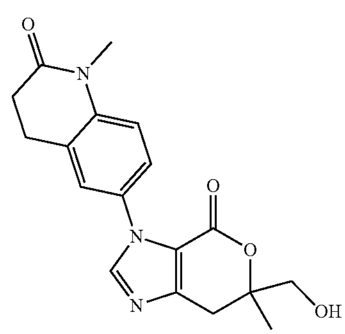 [SMILES: CN1C(=O)CCc2cc(-n3cnc4c3C(=O)OC(C)(CO)C4)ccc21] | 6-[(6R)-6-(hydroxymethyl)-6-methyl-4-oxo-3H,4H,6H,7H-pyrano[3,4-d]imidazol-3-yl]-1-methyl-1,2,3,4-tetrahydroquinolin-2-one |

TABLE 1-continued

| Compound | Structure | Name |
|---|---|---|
| 41 | 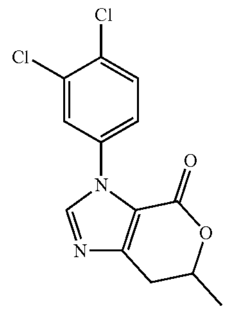 [SMILES: CC1Cc2ncn(-c3ccc(Cl)c(Cl)c3)c2C(=O)O1] | 3-(3,4-dichlorophenyl)-6-methyl-3H,4H,6H,7H-pyrano[3,4-d]imidazol-4-one |
| 42 | 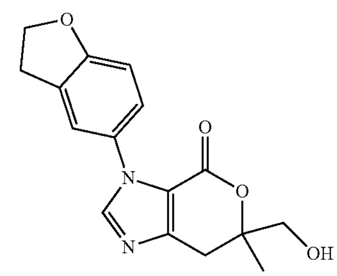 [SMILES: CC1(CO)Cc2ncn(-c3ccc4c(c3)CCO4)c2C(=O)O1] | 3-(2,3-Dihydro-benzofuran-5-yl)-6-hydroxymethyl-6-methyl-6,7-dihydro-3H-pyrano[3,4-d]imidazol-4-one |
| 43 | 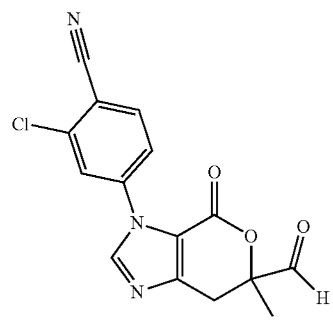 [SMILES: CC1(C=O)Cc2ncn(-c3ccc(C#N)c(Cl)c3)c2C(=O)O1] | 2-Chloro-4-(6-formyl-6-methyl-4-oxo-6,7-dihydro-4H-pyrano[3,4-d]imidazol-3-yl)-benzonitrile |
| 44 | 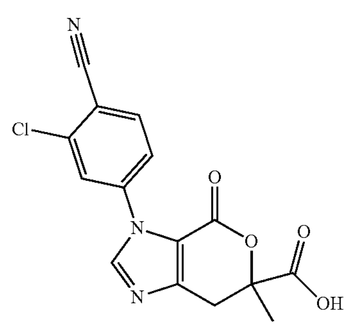 [SMILES: CC1(C(=O)O)Cc2ncn(-c3ccc(C#N)c(Cl)c3)c2C(=O)O1] | 3-(3-Chloro-4-cyano-phenyl)-6-methyl-4-oxo-3,4,6,7-tetrahydro-pyrano[3,4-d]imidazole-6-carboxylic acid |
| 45 | 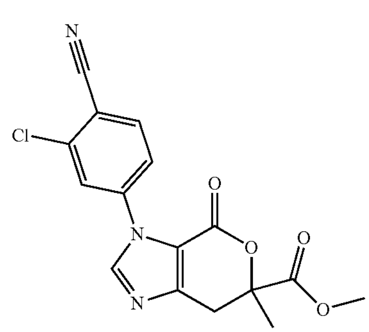 [SMILES: COC(=O)C1(C)Cc2ncn(-c3ccc(C#N)c(Cl)c3)c2C(=O)O1] | 3-(3-Chloro-4-cyano-phenyl)-6-methyl-4-oxo-3,4,6,7-tetrahydro-pyrano[3,4-d]imidazole-6-carboxylic acid methyl ester |

TABLE 1-continued

| Compound | Structure | Name |
|---|---|---|
| 46 | 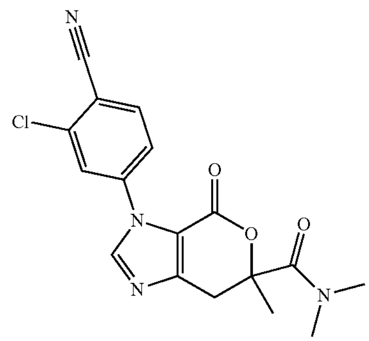 [SMILES: CN(C)C(=O)C1(C)Cc2ncn(-c3ccc(C#N)c(Cl)c3)c2C(=O)O1] | 3-(3-Chloro-4-cyano-phenyl)-6-methyl-4-oxo-3,4,6,7-tetrahydro-pyrano[3,4-d]imidazole-6-carboxylic acid dimethylamide |

In one embodiment, the methods of the invention relate to the use of compounds 1-46 depicted in Table 1 above, and the pharmaceutically acceptable salts thereof.

In another embodiment, the methods of the invention relate to the use of compounds 1-11, 13, 15, 18, 19, 22, 23, 26, 28, 29A, 29B, 30-33, 35, 39, 41, 42, 45 and 46 depicted in Table 1 above and the pharmaceutically acceptable salts thereof.

In one embodiment, the SLGT inhibitor used in the method of the invention is selected from the group consisting of empagliflozin, dapagliflozin and canagliflozin.

In another embodiment, the SLGT inhibitor used in the method of the invention is empagliflozin.

In another embodiment, the invention relates to methods for treating CKD comprising administering to a patient in need thereof a therapeutically effective amount of an AS inhibitor of the invention, or a pharmaceutically acceptable salt therefore, optionally in combination with empagliflozin.

In another embodiment, the invention relates to methods for treating CKD comprising administering to a patient in need thereof a therapeutically effective amount of an AS inhibitor of the invention, or a pharmaceutically acceptable salt therefore, in combination with empagliflozin.

DETAILED DESCRIPTION OF THE INVENTION

Abbreviations:

| | |
|---|---|
| ACE | Angiotensin-converting enzyme |
| ACTH | Adrenocorticotropic hormone |
| AKI | Acute kidney injury |
| ARB | Angiotensin receptor blocker |
| AS | Aldosterone synthase |
| BMI | Body mass index |
| CKD | Chronic kidney disease |
| CREDENCE | Canagliflozin and Renal Events in Diabetes with Established Nephropathy Clinical Evaluation |
| EMPA-REG | Empagliflozin Cardiovascular Outcome Event Trial in Type 2 Diabetes Mellitus Patients |
| ESRD | End stage renal disease |
| GFR | Glomerular filtration rate |
| INDT | Irbesartan Type II Diabetic Nephropathy Trial |
| LADA | Latent autoimmune diabetes in adults |
| MR | Mineralocorticoid receptor |
| NYHA | New York Heart Association |
| RAAS | Renin-angiotensin-aldosterone system |
| RENAAL | Reduction of Endpoints in NIDDM with the Angiotensin II Antagonist Losartan |
| SGLT2 | Sodium-glucose transport protein 2 |

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

Compounds of formula (I) also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The methods of the invention also include pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of formula (I).

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the compounds of formula (I) can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula (I) are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_3))$—, —$(CHCH(CH_3)_2)$— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. For example, the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated.

Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—Ra may be represented as phenyl-S(O)$_m$— when Ra is phenyl and where m is 0, 1 or 2.

General Synthetic Methods

The compounds of formula (I) used in the methods of the invention may be prepared by the methods and examples described in WO 2016/014736.

Methods of Therapeutic Use

Unless otherwise defined herein, the term "chronic kidney disease" or "CKD" refers to either kidney damage or a decreased glomerular filtration rate (GFR) of less than 60 mL/min/1.73 m2 for at least 3 months. The stage or severity of CKD is based on GFR values as described below:
  Stage 1: Kidney damage with normal or increased GFR (>90 mL/min/1.73 m 2)
  Stage 2: Mild reduction in GFR (60-89 mL/min/1.73 m 2)
  Stage 3a: Moderate reduction in GFR (45-59 mL/min/1.73 m 2)
  Stage 3b: Moderate reduction in GFR (30-44 mL/min/1.73 m 2)
  Stage 4: Severe reduction in GFR (15-29 mL/min/1.73 m 2)
  Stage 5: Kidney failure (GFR <15 mL/min/1.73 m 2 or dialysis)

As used herein, the term "end stage kidney disease" refers to either a kidney function decline below an eGFR of <15 mL/min/1.73 m2 and/or requires renal replacement therapy by kidney transplant or dialysis.

In one embodiment, the patient has Stage 1 CKD, or Stage 2, CDK, or Stage 3 CKD, or Stage 4 CKD, or Stage 5 CKD.

In another embodiment, the patient has end stage kidney disease.

In one embodiment, the invention relates to a method for treating, preventing, and/or reducing the risk of chronic kidney disease progression, end stage kidney disease, renal death or cardiovascular death in adult CKD patients who are at high risk for disease progression including fast progressing patients (e.g. eGFR decline of >3 ml/min/year), the method comprising administering a therapeutically effective amount of a compound of formula (I), or a pharmaceutically acceptable salt thereof, to a patient in need thereof, optionally in combination with empagliflozin.

In another embodiment, the CKD patient has or is at risk of eGFR decline of >3 ml/min/year.

In another embodiment, the invention relates to a method for treating, preventing, and/or reducing the risk of chronic kidney disease progression, end stage kidney disease, renal death or cardiovascular death in adult patients, the method comprising administering to a patient in need therefore a therapeutically effective amount of a compound of formula (I), or a pharmaceutically acceptable salt thereof, optionally in combination with empagliflozin.

Direct inhibition of AS has the potential to reduce the deleterious effects caused by both the MR-dependent and MR-independent actions of aldosterone. Since AS inhibitors affect MR-dependent actions, there is a potential risk for hyperkalaemia. Accordingly, another aspect of the clinical trial relates to the treatment of CKD with an AS inhibitor in combination with an SGLT2 inhibitor empagliflozin. The combination treatment with an SGLT2 inhibitor mitigates the hyperkalaemia of certain AS inhibitors, thereby allowing for a higher dose of the AS inhibitor with balanced safety for hyperkalaemia. This dual mechanism is also expected to provide a greater therapeutic benefit than mineralocorticoid receptor (MR) antagonists, with less risk of hyperkalaemia because efficacy should be elicited at doses corresponding to a lesser impact on MR-dependent electrolyte regulation. In one embodiment, the SGLT2 inhibitor is empagliflozin.

In one embodiment, the invention relates to a method for treating, preventing, and/or reducing the risk of kidney disease progression, end stage kidney disease, renal death or cardiovascular death in adult patients, the method comprising administering to a patient in need thereof a therapeutically effective amount of a compound of formula (I), or a pharmaceutically acceptable salt thereof, in combination with empagliflozin.

In another embodiment, the invention relates to a method for treating, preventing, and/or reducing the risk of kidney disease progression, end stage kidney disease, renal death or cardiovascular death in adult patients with uncontrolled CKD progression (eGFR decline of >3 ml/min/1.73m2/y), the method comprising administering to a patient in need therefore a therapeutically effective amount of a compound of formula (I), or a pharmaceutically acceptable salt thereof, in combination with empagliflozin.

In another embodiment, the invention relates to a method of treating, preventing, and/or reducing the risk of kidney disease progression, end stage kidney disease, renal death or cardiovascular death in adult patients, the method comprising administering to a patient in need thereof a therapeutically effective amount of a compound of formula (I), or a pharmaceutically acceptable salt thereof, in combination with empagliflozin, wherein the treatment with empagliflozin reduces the risk of hyperkalaemia as compared to patients treated without empagliflozin.

In another embodiment, a compound of formula (I), or a pharmaceutically acceptable salt thereof, may be used for the preparation of a medicament for treating chronic kidney disease; in another embodiment, the medicament comprises an SGLT2 inhibitor; in an another embodiment, the medicament comprises an SGLT2 inhibitor which is empagliflozin.

For therapeutic use, each of the compounds of formula (I) and the SGLT2inhibitor may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compound of formula (I), and optionally an SGLT2 inhibitor, may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, each of the dosage forms of the compound of formula (I) of this invention and the optional SGLT2inhibitor may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)).

Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Within this invention it is to be understood that the combinations or combined uses of an AS inhibitor and SGLT2inhibitor according to this invention may envisage the simultaneous, sequential or separate administration of the therapeutic components.

In this context, "combination" or "combined" within the meaning of this invention may include, without being limited, fixed and non-fixed (e.g. free) forms (including kits, or other administration, application or dosage forms) and uses, such as e.g. the simultaneous, sequential or separate use of the AS inhibitor and SGLT2inhibitor.

The combined administration or application of this invention may take place by administering the therapeutic components together, such as e.g. by administering them simultaneously in one single or in two separate formulations. Alternatively, the administration may take place by administering the therapeutic components sequentially, such as e.g. successively in two separate formulations.

For the combination therapy of this invention the therapeutic components may be administered separately (which implies that they are formulated separately) or formulated altogether (which implies that they are formulated in the same preparation). Hence, the administration of one element of the combination of the present invention may be prior to, concurrent to, or subsequent to the administration of the other element of the combination.

In another aspect of the invention, patients may optionally be treated with a third therapeutic agent. Non limiting examples of optional third therapeutic agents ACE inhibitors and ARBs.

Nonlimiting examples of ACE inhibitors include benazepril, captopril, enalapril, fosinopril, lisinopril, moexipril, perindopril, quinapril, ramipril and trandolapril. Nonlimiting examples of ARBs include irbesartan, losartan, telmisartan and valsartan.

Clinical Trial Protocol

The efficacy and safety of the compounds of formula (I), alone and in combination with an SGLT2inhibitor, is studied according the following clinical trial protocol. In summary, patients are administered one of three doses of an AS inhibitor over 14 weeks. In this phase II dose-finding trial, the AS inhibitor is used alone and in combination with empagliflozin, in male and female patients with diabetic and non-diabetic CKD.

Trial Endpoints:

The primary endpoint is the change from baseline in log transformed Urine Albumin Creatinine Ratio (UACR) measured in First Morning Void urine after 14 weeks.

Secondary Endpoints:
UACR response I, defined as a decrease of at least 30% absolute change in First Morning Void urine of UACR from baseline to 14 weeks.
UACR response II, defined as a decrease of at least 15% absolute change in First Morning Void urine of UACR from baseline to 14 weeks Trial Design Randomised, double-blind, parallel dose group, placebo-controlled phase II clinical trial to investigate the effect of three doses of the AS inhibitor alone and in combination with empagliflozin over 14 weeks in patients with diabetic and non-diabetic chronic kidney disease. The trial will include a 1:1 randomised run-in period of 8 weeks for empagliflozin 10 mg/placebo followed by a randomised treatment period of 14 weeks for the AS inhibitor/placebo alone or in combination with empagliflozin.

Total number of patients randomized: At least, 552.

Number of patients per treatment group: A minimum of 60 patients completed per arm in the Treatment Period, overall 480 completed patients.

Diagnosis: Diabetic or non-diabetic Chronic Kidney Disease

Main Inclusion and Exclusion Criteria:

Inclusion:
  Male or female patients aged ≥18 years at time of consent.
  eGFR ≥30 and <90 mL/min/1.73 $m^2$.
  UACR ≥200 and <5000 mg/g.
  Stable treatment with either ACEi or ARB (not both).
  Serum potassium ≤4.8 mmol/L Exclusion:
  Current or planned SGLT2 inhibitor/SGLT-1/2 inhibitor treatment
  Type 1 Diabetes Mellitus Test Product(s): AS Inhibitor and Empagliflozin Dose:
  AS inhibitor 3 mg daily (QD) or 10 mg daily (QD) or 20 mg daily (QD)
  Empagliflozin 10 mg daily (QD)
  Mode of administration: p.o. (taken by the mouth)
  Comparator product(s): Placebo matching each dose of the AS inhibitor and empagliflozin Dose: Not applicable
  Mode of administration: p.o.
  Duration of treatment: 14 weeks (8 weeks run-in with empagliflozin/placebo and 14 weeks of treatment with the AS inhibitor/placebo alone or in combination with empagliflozin/placebo)

Statistical methods: A mixed-effect model for repeated measures (MMRM) will be used to obtain adjusted mean changes from baseline for the treatment effects of continuous endpoints. This MMRM model will include fixed effect of treatment as categorical variable, and fixed effect of baseline at each visit as continuous variable. Visit will be considered as repeated measures with an unstructured covariance structure for the within-patient variability. For dose-finding, predicted average response for each dose group and the estimated covariance matrix from the MMRM will be used in the multiple comparison procedures and modelling (MCPMod) analysis. Several possible dose-response patterns will be evaluated in the MCPMod to identify the best-fitting model and optimal dose for further development.

The trial will compare 3 doses of the AS inhibitor with placebo in patients with diabetic and nondiabetic CKD randomised to empagliflozin or placebo as background therapy (established during the randomised run-in).

The trial will characterise the dose-response curve for the AS inhibitor in patients with diabetic and non-diabetic CKD by assessing 3 doses and placebo. The response is the change from treatment period baseline in log-transformed UACR measured in First Morning Void urine after 14 weeks. The primary objectives are (1) to demonstrate a non-flat dose response curve, evaluate the quantitative treatment effect size and evaluate the dose-response relationship, (2) to determine an optimal dose of the AS inhibitor by comparing the change from treatment period baseline in log-transformed UACR measured in First Morning Void urine after 14 weeks between the 3 doses of the AS inhibitor and placebo.

One set of secondary objectives will be as above but in subpopulations of (1) placebo background therapy (2) empagliflozin background therapy.

These analyses will include all data prior to AS inhibitor discontinuation, down-titration of the AS inhibitor, or death, regardless of change in concurrent SGLT2-inhibitor use.

Primary Endpoint(s)

Change from treatment period baseline in log transformed Urine Albumin Creatinine Ratio (UACR) measured in First Morning Void urine after 14 weeks.

Secondary Endpoint(s)
  UACR response I, defined as decrease of at least 30% absolute change in First Morning
  Void urine of UACR from treatment period baseline to 14 weeks.
  UACR response II, defined as decrease of at least 15% absolute change in First Morning Void urine of UACR from treatment period baseline to 14 weeks.

Further Objectives

Further objectives include the efficacy, safety, PK and PD of three doses of the AS inhibitor compared with placebo after 14 weeks of trial treatment in patients with CKD.

Further Endpoints
  Change from baseline in eGFR after 14 weeks.
  eGFR slope.
  Change from baseline in serum potassium after 14 weeks
  Change from baseline in blood pressure and pulse after 14 weeks
  Change from baseline in body weight after 14 weeks.

Further endpoints include changes from baseline in plasma aldosterone, its precursors corticosterone and 11-deoxycorticosterone, cortisol and its precursor 11-deoxycortisol to assess target engagement and target selectivity; this includes the comparison between selected visits of time profiles of these markers (serial measurements over 2 to 3 hours largely corresponding to the PK sampling timepoints for the AS inhibitor). Further endpoints also include changes from baseline in biomarkers that represent the key mechanisms of kidney pathophysiology, such as inflammation, fibrosis, tubulo-interstitial injury, oxidative stress, glomerular injury, and endothelial dysfunction.

PK Parameters Will be Assessed as Further Endpoints.

In the context of endpoints, the term "baseline" refers to the last observation prior to the first intake of the AS inhibitor trial medication in the Treatment Period, with the exception of First Morning Void, where baseline is defined as the mean of all non-missing assessments from Week −2 in the Randomised Run-in Period until prior to the first intake of trial medication in the Treatment Period. This does not include the UACR measured in spot urine at Screening. More details and additional further endpoints may be defined in the trial statistical analysis plan (TSAP).

Description of Design and Trial Population

Overall Trial Design

This trial is a multicentre, randomised, double-blind, parallel dose group, placebo-controlled phase II clinical trial to investigate the effect of three doses of the AS inhibitor alone, and in combination with empagliflozin, in patients with diabetic and non-diabetic CKD who are on background treatment with either ACEi or ARB. Empagliflozin versus placebo use will be established during a 1:1 randomised run-in period.

Patients will be screened in the trial once they have signed the informed consent. They will undergo a screening period of up to 2 weeks from the time of the first screening assessment. After their eligibility has been confirmed at screening, patients will enter the Randomised Run-in Period. Patients will be randomised equally to receive either empagliflozin 10 mg or placebo matching to empagliflozin 10 mg in a 1:1 ratio and will continue taking the assigned study treatment for 8 weeks. After 8 weeks of treatment in the Run-in Period, patients will enter the Treatment Period. Patients who received empagliflozin in the Run-in Period will be randomised equally into one of four parallel dose groups in a 1:1:1:1 ratio to receive one of 3 doses of the AS inhibitor (3 mg QD, 10 mg QD or 20 mg QD) in combination with empagliflozin, or empagliflozin alone (empagliflozin plus placebo matching to the AS inhibitor). Patients who received placebo in the Run-in Period will be randomised equally into one of four parallel dose groups in a 1:1:1:1 ratio to receive one of 3 doses of the AS inhibitor (3 mg QD, 10 mg QD or 20 mg QD) or placebo. Patients will continue receiving the assigned treatment for 14 weeks.

The study will be blinded to both empagliflozin and the AS inhibitor. As the AS inhibitor film coated tablets of the different dose strengths (3 and 10 mg) and empagliflozin have different dimensions, in order to minimize possible observer bias and ensure the study is blinded across dose groups the patients will each take 4 tablets a day during the Treatment Period.

Eligible patients will be randomised to treatment using a stratification algorithm that helps ensure balance between the treatment groups with respect to prognostic variables such as: prior diabetes, eGFR and UACR. A minimum of 40% of patients will be required to be randomised during the run-in period in each of the disease types: diabetic kidney disease and non-diabetic kidney disease. Patients with diabetes may have diabetic kidney disease, nondiabetic CKD aetiologies, or a combination; for the purpose of stratification they will be classed as having diabetic kidney disease.

From the start of the screening until the end of the trial, at various time points patients will collect their urine for UACR analysis. First morning void urine will be collected before the daily dose of study medication. For each time point where a physical visit to the site is not foreseen, the patient will be equipped with urine collection containers to sample urine from their First Morning Voids. To decrease the burden on patients, where country regulations allow, samples taken at home between visits will be shipped from the patient's home to a central laboratory for analysis. Where this is not possible alternative arrangements will be made, e.g. samples taken to the investigational site. Samples taken directly prior to a physical visit at the site will be taken to the site to be processed by the site staff.

Beyond analysis for safety, urine and blood samples in this trial will serve for biomarker analysis including UACR.

Following the Treatment Period, or at the time trial treatment in the Run-in Period or the Treatment Period is permanently discontinued, patients will have an End of Treatment (EoT) visit. This will be followed by a 4-week follow-up period off-treatment. A first follow-up visit (FUp1) at least 7 days later is considered as the end of the Residual Effect Period (REP). Until the end of REP all AEs and changes to concomitant medication need to be collected, documented and reported. Patients who discontinue prematurely during the Run-In Period must attend FUp1 at least. All other patients should be encouraged to complete the full follow-up period.

During the follow-up period the patient will not be treated with trial medication, but should, if possible, continue with any background treatment they are on, and will collect additional urine at home. After the 4-week follow-up period the patient will have a final visit where again blood and urine samples will be collected. With the conclusion of this visit the trial participation is complete for the individual patient.

A rise in serum potassium and a drop in eGFR under treatment with the AS inhibitor cannot be excluded. Therefore, patients will be monitored closely (weekly for 2 weeks) after starting treatment with the AS inhibitor or matching placebo, and regularly thereafter. In order to be able to address future scientific questions, patients will be asked to voluntarily donate biospecimens for banking. If the patient agrees, banked samples may be used for future biomarker research and drug development projects, e.g. to identify patients that are more likely to benefit from a treatment or experience an adverse event (AE), or to gain a mechanistic or genetic understanding of drug effects and thereby better match patients with therapies.

Historical kidney-related data (including serum creatinine data, eGFR values and historical AKI data) will be collected in the trial over a period of 3 years before start of treatment. This may be used in future to explore the benefit of AS inhibitor in patients with different categories of rate of CKD progression.

Discussion of Trial Design, Including the Choice of Control Group(s) This dose-finding trial has been designed to assess efficacy and safety of the AS inhibitor alone, and in combination with empagliflozin, as likely initiated in clinical practice. It also allows the opportunity to find the optimal dose of the AS inhibitor to be used for future development, on its own and/or as a fixed dose combination with empagliflozin.

Patients will initially start on 8 weeks of empagliflozin or placebo in the Randomised Run-in Period and will then receive 14 weeks of treatment with the AS inhibitor or placebo in the Treatment Period in addition to the empagliflozin or placebo treatment. It is important that patients run in on empagliflozin first, before starting treatment with the AS inhibitor, for safety reasons since both drugs have potentially similar haemodynamic effects. 8 weeks of empagliflozin treatment is considered sufficient to reach stable haemodynamic levels, before starting with the AS inhibitor.

A parallel group design was chosen to investigate three different dose regimens of the AS inhibitor alone and in combination with empagliflozin. The first parallel group will investigate three different dose regimens of the AS inhibitor and placebo. The second parallel group will investigate three different dose regimens of the AS inhibitor, in combination with empagliflozin, versus empagliflozin+placebo. Placebo is used to control for observer and subject bias, and randomisation to control for assignment bias.

The study design involves two randomisations. The first run-in randomisation to empagliflozin and placebo is required for two purposes. Firstly, the run-in randomization will ensure an equally distributed patient population to the empagliflozin and placebo groups followed by second randomisation to treatment groups. Secondly, a staggered approach starting empagliflozin during the run-in period, followed by later initiation of the AS inhibitor was chosen to enhance patient safety. Both, empagliflozin and the AS inhibitor, have a haemodynamic effect which leads to an acute eGFR decrease. Staggered treatment initiation is planned to reduce such effect.

UACR was chosen as primary endpoint (First Morning Void collection) and secondary endpoint (responder rate) because it was shown in previous phase II trials by others in CKD that it is sensitive, differentiating different doses, broad in its dynamic range and reaching a stable plateau within a reasonable time after start of treatment. It has been accepted by authorities as dose finding biomarker in CKD. Furthermore, the change in UACR correlates with long-term clinical and patient relevant outcomes.

Since UACR is a parameter that varies intra-individually over time, multiple measurements are required at treatment period baseline and during the treatment period especially towards the end of treatment where a stable response to the drug should be achieved. UACR measurements will therefore be collected on 2 consecutive days at 3 timepoints (6 measurements in total) from Week −2 to Week 0 for treatment period baseline, and from Week 12 to Week 14 during the treatment period. Sequential collection of urine during a 4-week follow-up period may deliver exploratory results of response stability and potential rebound effects.

To further characterise haemodynamic effects, serum creatinine will be measured at regular intervals for exploratory analysis.

A data monitoring committee (DMC) will be established to review safety data at regular intervals.

Selection of Trial Population

It is expected that at least 552 patients will be randomised to the Randomised Run-in Period from approximately 200 sites. Investigators are expected to be nephrologists, endocrinologists or general practitioners. Screening of patients for this trial is competitive, i.e. screening for the trial will stop at all sites at the same time once a sufficient number of patients has been screened. Investigators will be notified about screening completion and will then not be allowed to screen additional patients for this trial. Patients already in screening at this time will be allowed to continue to randomisation if eligible. A minimum of 552 patients will be randomised to the Run-in Period to ensure that at least 480 will complete the study treatment in order to preserve the trial power by increasing sample size. If, during the study conduct, the dropout rate is higher than projected, recruitment may continue until the required number of patients complete treatment. A log of all patients enrolled into the trial (i.e. who have signed informed consent) will be maintained in the Investigator Site File (ISF) irrespective of whether they have been treated with investigational drug or not.

If a patient has been randomised in error (=did not meet all inclusion criteria or met one or more exclusion criteria), the sponsor or delegate should be contacted immediately. Based on an individual benefit-risk assessment a decision will be made whether continued trial participation is possible or not.

Main Diagnosis for Trial Entry

Chronic Kidney Disease.

If the investigator judges that the participant must receive empagliflozin (or any other SGLT-2 or SGLT-1/2 inhibitor) in the context of prevailing local, national or international guidance, the patient should not be included in the trial due to the risk the patient may be assigned to placebo alone in the trial.

No potential participant currently being treated with empagliflozin (or other SGLT2 or SGLT-1/2 inhibitor) should be taken off this therapy to meet the eligibility criteria.

Inclusion Criteria

1. Signed and dated written informed consent in accordance with ICH-GCP and local legislation prior to admission to the trial.
2. Male or female patients aged ≥18 years at time of consent.
3. eGFR (Chronic Kidney Disease Epidemiology Collaboration [CKD-EPI] formula) ≥30 and <90 mL/min/1.73 m2 at Visit 1 by central laboratory analysis.
4. UACR≥200 and <5,000 mg/g in spot urine (midstream urine sample) by central laboratory analysis at Visit 1.1
5. If the patient is taking any of the following medications they should be on a stable dose for at least 4 weeks prior to visit 1 and until first randomisation prior to run-in with no planned change of the therapy during the trial: anti-hypertensives, NSAIDs, endothelin receptor antagonists, low dose systemic steroids (e.g. prednisolone ≤10 mg or equivalent).
6. Treatment with a clinically appropriate, stable dose of either ACEi or ARB (but not both together), for ≥4 weeks prior to visit 1 and until first randomisation with no planned change of the therapy during the trial.
7. In the Investigator's opinion, one or more of the following underlying kidney disease causes:
   Diabetic kidney disease. These patients must have type 2 diabetes mellitus and
   their treatment (including GLP1 receptor agonist) should be unchanged or
   changes deemed minor (according to investigator's judgement) within 4 weeks
   prior to Visit 1 and until first randomisation.
   Hypertensive kidney disease
   Chronic glomerulonephritis defined as one of the following:
   IgA nephropathy,
   Membranous nephropathy
   Focal Segmental Glomerulosclerosis (FSGS)
8. Glycated Haemoglobin (HbA1c)<10.0% at Visit 1 measured by the central laboratory.
9. Serum potassium ≤4.8 mmol/L at Visit 1 measured by the central laboratory.
10. Seated SBP≥110 and ≤160 mmHg and DBP≥65 and ≤110 mmHg at Visit 1 (mean values from three BP measurements) and optimised anti-hypertensive treatment according to local standard of care and investigator's judgement.
11. Body Mass Index (BMI) ≥18.5 and <50 kg/m2 at Visit 1.
12. Women of child-bearing potential2 (WOCBP) must be ready and able to use highly effective methods of birth control. Such methods should be used throughout the trial. Men must be vasectomised or willing and able to use a condom if their partner is a WOCBP.

Additional Inclusion Criteria to be Assessed Before Second Randomisation (Start of Treatment Period):

1. Serum potassium ≤4.8 mmol/L measured by local or central laboratory within 7 days prior to randomisation to the Treatment Period.
2. eGFR (Chronic Kidney Disease Epidemiology Collaboration [CKD-EPI] formula) ≥20 mL/min/1.73 m2 measured by local or central laboratory within 7 days prior to randomisation to the Treatment Period.

Exclusion Criteria

1. Treatment with inhibitors of aldosterone mediated effects (e.g., mineralocorticoid receptor antagonists such as spironolactone), or intake of other potassium sparing diuretics (e.g., amiloride) within 7 days prior to first randomisation or planned during trial treatment phase.
2. Treatment with other Renin Angiotensin Aldosterone System (RAAS) interventions (apart from either ACEi or ARB) within 4 weeks prior to Visit 1 and throughout screening or planned during the trial. Patients who must or wish to continue the intake of restricted medications or any drug considered likely to interfere with the safe conduct of the trial are also excluded.
3. Type 1 diabetes mellitus, or history of other autoimmune causes of diabetes mellitus (e.g. LADA)
4. Patients at increased risk of ketoacidosis in the opinion of the investigator.
5. Currently receiving SGLT2 or SGLT1/2 inhibitor or planned initiation during the trial.
6. Use of biotin (Vitamin B7, Vitamin H, or coenzyme R) at doses ≥5 mg/day (including food supplements) within 72 hours of Visit 1 or planned during the trial.
7. Absolute cortisol value of <18 µg/dL (496.6 nmol/L) 30 minutes (±5 min) after injection of ACTH, at Visit 1, as measured by local or central laboratory.
8. Known history of severe symptomatic orthostatic dysregulation as judged by the investigator before first randomisation.[3]
9. Intermittent or persistent 2nd or 3rd degree atrioventricular block, sinus node dysfunction with clinically significant bradycardia or sinus pauses, not treated with a pacemaker.
10. Serum cortisol <5 µg/dL (138.0 nmol/L) or any clinically relevant abnormal laboratory value, at Visit 1 or until first randomisation, which in the investigator's judgement puts the patient at additional risk.
11. Any immunosuppression therapy or immunotherapy in the last 3 months prior to Visit 1. This also applies to systemic steroids except oral prednisolone ≤10 mg or equivalent.
12. Acute kidney injury (AKI) according to the Kidney Disease: Improving Global Outcomes (KDIGO) definition in the 30 days prior to Visit 1 or until first randomisation.
13. End stage kidney disease, maintenance dialysis, functioning kidney transplant at Visit 1 or before first randomisation; planned kidney transplant or chronic renal replacement therapy during the trial.
14. Heart failure, patients with NYHA III/IV or coronary heart disease not compensated by medical treatment.
15. Active infection with SARS-CoV-2 from Visit 1 until first randomisation, or a positive acute infection confirmatory test within 4 weeks prior to Visit 1.
16. Any documented active or suspected malignancy at the time of screening or history of confirmed malignancy within two years prior to Visit 1 (except appropriately treated basal cell carcinoma of the skin, in situ carcinoma of uterine cervix, and prostatic cancer of low grade [T1 or T2]) or treatment for cancer within 2 years prior to Visit 1.
17. Major surgery (investigator's judgement) planned during the trial.
18. History of clinically relevant allergy/hypersensitivity that would interfere with trial participation including allergy to investigational product/placebo/tetracosactide (injection for ACTH test) or their excipients (e.g. lactose monohydrate).
19. Any other medical condition that in the investigator's opinion poses a safety risk for the patient or may interfere with the trial objectives.
20. Previous randomisation in this trial.
21. Currently enrolled in another investigational device or drug trial, or less than 30 days or 5 half-lives (whichever is longer) prior to Visit 1 since ending another investigational device or drug trial(s) or receiving other investigational treatment(s).
22. Chronic alcohol or drug abuse or any condition that, in the investigator's opinion, makes them an unreliable trial participant or unlikely to complete the trial.
23. Women who are pregnant, nursing or who plan to become pregnant while in the trial.

Discontinuation of Patients from Treatment

Patients may discontinue trial treatment or withdraw consent to trial participation as a whole ("withdrawal of consent") with very different implications as described below. Every effort should be made to keep the patients in the trial: if possible on treatment. Measures to control the withdrawal rate include careful patient selection, appropriate explanation of the trial requirements and procedures prior to trial enrolment, as well as the explanation of the consequences of withdrawal. The decision to discontinue trial treatment or withdraw consent to trial participation and the reason must be documented in the patient files and CRF. If applicable, consider the requirements for Adverse Event collection reporting.

Discontinuation of Trial Treatment

Permanent Discontinuation

An individual patient will permanently discontinue all randomised trial treatment if:

1. The patient develops Acute Kidney Injury as per clinical judgement by the investigator and/or according to the Kidney Disease: Improving Global Outcomes (KDIGO) definition (see Kidney Disease: Improving Global Outcomes (KDIGO) Acute Kidney Injury Work Group; KIDGO clinical practice guideline for acute kidney injury. Kidney Int Suppl 2012; 2(1); 1-138.)
2. The patient experiences a drop in eGFR:
    ≥30% within one week of starting treatment in the Treatment Period; and/or
    ≥40% at any time since start of the Treatment Period
3. The patient progresses to end stage kidney disease defined by either a kidney function decline below an eGFR of <15 mL/min/1.73 m2 and/or requires renal replacement therapy by kidney transplant or dialysis.
4. The patient wants to discontinue trial treatment. The patient will be asked to explain the reasons but has the right to refuse to answer.
5. The patient has repeatedly shown to be non-compliant with important trial procedures and, in the opinion of both the investigator and sponsor representative, the safety of the patient cannot be guaranteed as he/she is not willing or able to adhere to the trial requirements in the future.
6. The patient needs to take concomitant medication that is not permitted. However, if the patient needs to modify a dose, where a stable dose is permitted only, this will not automatically require a discontinuation. In this case the sponsor should be consulted.
7. The patient can no longer receive trial treatment for medical reasons such as surgery, serious or severe Drug Induced Liver Injury attributable to the trial drug, other adverse events, or other diseases.
8. The patient requires treatment for cancer. Some exclusions apply e.g. for Basal Cell Carcinoma—please discuss with sponsor.
9. A female patient becomes pregnant. The patient will be followed up until birth or otherwise termination of the pregnancy.

An individual patient will permanently discontinue AS inhibitor/placebo if:

1. The patient's serum potassium measures ≥6.0 mmol/L by central or any local laboratory, or ≥5.6 mmol/L if down-titration is considered inappropriate.

2. The patient develops Cushing's syndrome, adrenal insufficiency (including cortisol level <18 µg/dL 30 min (±5 min) after ACTH application) or the patient's cortisol level is <3 µg/dL (82.8 nmol/L) at any point in the trial. The patient should be followed according to local guidelines until resolution of the event and the event should be reported to the sponsor.

An individual patient will permanently discontinue empagliflozin/placebo if:
1. Ketoacidosis is suspected.
2. Fournier's gangrene is suspected.

In these cases, if one of the study medications (either empagliflozin/placebo or AS inhibitor/placebo) is permanently discontinued, the patient may continue to receive treatment with the other study medication.

Treatment Interruption

In the following case, all randomised study medication must be interrupted:
severe SARS-COV-2 infection In the following cases, the empagliflozin/placebo must be interrupted:
complicated UTI
symptomatic volume depletion In the following cases, the AS inhibitor/placebo must be interrupted:
serum potassium ≥5.6 mmol/L
serum potassium ≥5 mmol/L if the patient is unable or unwilling to return to the investigational site In these cases, trial treatment could be restarted upon recovery if medically justified.

NONLIMITING EMBODIMENTS OF THE INVENTIONS

What is Claimed is:

Embodiment 1. A method for treating diabetic and non-diabetic chronic kidney disease (CKD), the method comprising administering to a patient in need thereof a pharmaceutically effective amount of a compound of formula (I)

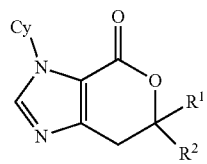

I or a pharmaceutically acceptable salt thereof, wherein:
Cy is a monocyclic or bicyclic ring system selected from $C_{3-10}$cycloalkyl, heterocyclyl, aryl and heteroaryl,
wherein each of the said $C_{3-10}$cycloalkyl, heterocyclyl, aryl and heteroaryl groups is optionally and independently substituted with one, two, or three substituent groups selected from halogen, —$C_{1-3}$-alkyl, —$OC_{1-3}$-alkyl, —$CF_3$, cyano, oxo, —$N(C_{1-3}$-alkyl$)_2$, —$NH(C_{1-3}$-alkyl), —$NHCOC_{1-3}$-alkyl, —$C(O)C_{1-3}$-alkyl, —$C(O)OC_{1-3}$alkyl, hydroxy$C_{1-3}$alkyl, or heteroaryl; and $R^1$ and $R^2$ are independently selected from H, $C_{1-3}$alkyl, hydroxy$C_{1-3}$alkyl, —$CH_2NHC(O)OC_{1-4}$alkyl, —$CH_2OC(O)C_{1-4}$alkyl, —$C(O)OC_{1-4}$alkyl, —$C(O)H$, —COOH, —$C(O)NHC_{1-4}$-alkyl and $C(O)N(C_{1-4}$-alkyl$)_2$; or $R^1$ and $R^2$ taken together form a $C_{3-6}$cycloalkyl or $C_{3-6}$-heterocyclyl.

Embodiment 2: The method of Embodiment 1, wherein:
Cy is a phenyl, cyclohexyl, indanyl, 2,3-dihydrobenzofuranyl or tetrahydroquinolinyl group, each optionally substituted with one, two, or three substituent groups independently selected from —Cl, —F, $C_{1-3}$alkyl, oxo and CN; and $R^1$ and $R^2$ are independently selected from H, $C_{1-3}$alkyl, hydroxy$C_{1-3}$alkyl, —$CH_2NHC(O)OC_{1-4}$alkyl, —$C(O)N(C_{1-4}$-alkyl$)_2$ and —$CH_2OC(O)C_{1-4}$alkyl.

Embodiment 3: The method of Embodiment 1, wherein:
Cy is phenyl optionally substituted with one, two, or three substituent groups independently selected from —Cl, —F, $C_{1-3}$alkyl and CN.

Embodiment 4: The method of Embodiment 1, wherein:
Cy is phenyl substituted with CN and optionally substituted with one or two additional groups independently selected from —Cl, —F and $C_{1-3}$alkyl;
$R^1$ is —$CH_3$; and
$R^2$ is —$CH_3$ or —$CH_2OH$.

Embodiment 5: The method of Embodiment 4, wherein:
$R^2$ is —$CH_2OH$.

Embodiment 6: The method of Embodiment 4, wherein:
$R^2$ is —$CH_3$.

Embodiment 7: The method of Embodiment 1, wherein the compound of formula (I) is selected from the group consisting of compounds 1 to 46, or a pharmaceutically acceptable salt thereof.

Embodiment 8: The method of Embodiment 7, wherein the compound of formula (I) is selected from the group consisting of compound numbers 1-11, 13, 15, 18, 19, 22, 23, 26, 28, 29A, 29B, 30-33, 35, 39, 41, 42, 45 and 46.

Embodiment 9: The method of Embodiment 7, wherein the compound of formula (I) is

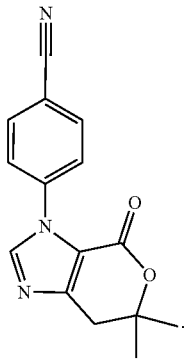 [SMILES: CC1(C)Cc2ncn(-c3ccc(C#N)cc3)c2C(=O)O1]

Embodiment 10: The method of Embodiment 7, wherein the compound of formula (I) is

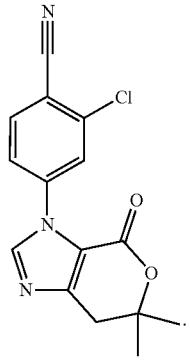 [SMILES: CC1(C)Cc2ncn(-c3ccc(C#N)c(Cl)c3)c2C(=O)O1]

Embodiment 11: The method of Embodiment 7, wherein the compound of formula (I) is

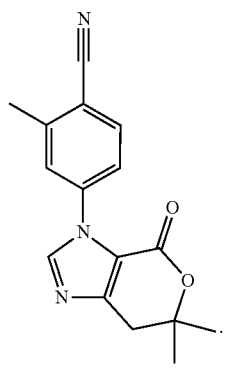

Embodiment 12: The method of Embodiment 7, wherein the compound of formula (I) is

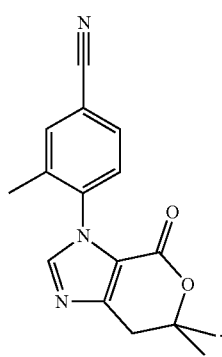

Embodiment 13: The method of Embodiment 7, wherein the compound of formula (I) is

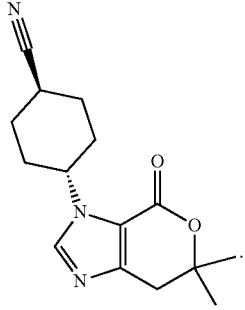 [SMILES: CC1(C)Cc2ncn([C@H]3CC[C@H](C#N)CC3)c2C(=O)O1]

Embodiment 14: The method of Embodiment 7, wherein the compound of formula (I) is

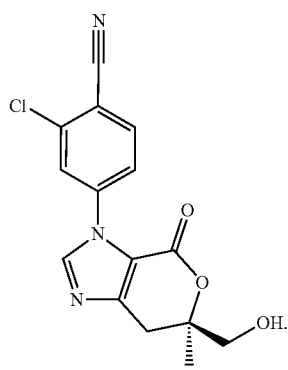 [SMILES: C[C@]1(CO)Cc2ncn(-c3ccc(C#N)c(Cl)c3)c2C(=O)O1]

Embodiment 15: The method of Embodiment 7, wherein the compound of formula (I) is

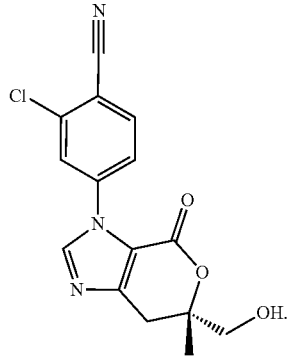 [SMILES: C[C@@]1(CO)Cc2ncn(-c3ccc(C#N)c(Cl)c3)c2C(=O)O1]

Embodiment 16: The method of Embodiment 7, wherein the compound of formula (I) is

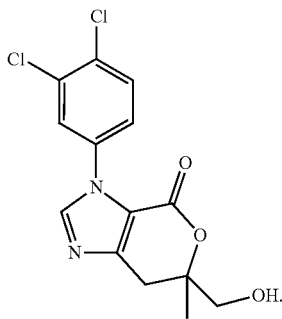 [SMILES: CC1(CO)Cc2ncn(-c3ccc(Cl)c(Cl)c3)c2C(=O)O1]

Embodiment 17: The method of Embodiment 7, wherein the compound of formula (I) is

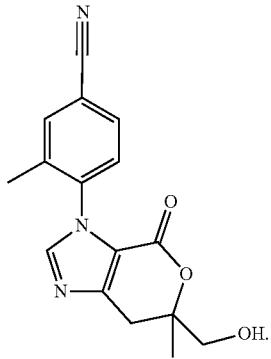 [SMILES: Cc1cc(C#N)ccc1-n1cnc2c1C(=O)OC(C)(CO)C2]

Embodiment 18: The method of Embodiment 7, wherein the compound of formula (I) is

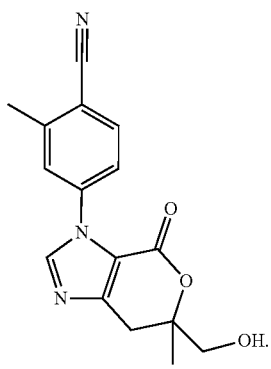 [SMILES: Cc1cc(-n2cnc3c2C(=O)OC(C)(CO)C3)ccc1C#N]

Embodiment 19: The method according to any of the preceding Embodiments, wherein the disease is diabetic chronic kidney disease.

Embodiment 20: The method according to any of Embodiments 1-18, wherein the disease is non-diabetic chronic kidney disease.

Embodiment 21: The method according to any one of Embodiments 1 to 20, wherein the patient has Stage 1 CKD, or Stage 2, CDK, or Stage 3 CKD, or Stage 4 CKD, or Stage 5 CKD.

Embodiment 22: The method according to any one of Embodiments 1 to 21, further comprising administering to the patient a pharmaceutically effective amount of a SGLT2 inhibitor, or a pharmaceutically acceptable salt thereof.

Embodiment 23: The method according to any of one the Embodiments 1 to 22, wherein the SGLT2 inhibitor is empagliflozin.

Embodiment 24: The method according to any one of Embodiments 1 to 23, wherein the AS inhibitor is administered in a daily amount of from 0.1 to 100 mg; or from 0.1 to 30 mg; or from 1 mg to 25 mg; or from 3 mg to 20 mg.

Embodiment 25: The method according to any one of Embodiments 1 to 24, wherein the AS inhibitor is administered in a daily amount of 3 mg, or 10 mg, 20 mg.

Embodiment 26: The method according to Embodiment 23, wherein the empagliflozin is administered in a daily amount of 10 mg or 25 mg.

Embodiment 27: The method according to Embodiment 30, wherein the empagliflozin is administered in a daily amount of 10 mg.

Embodiment 28: The method according to Embodiment 23, wherein the aldosterone synthase inhibitor is administered once daily in an amount of 3 mg, or 10 mg, or 20 mg; and the empagliflozin is administered in once daily in an amount of 10 mg.

Embodiment 29: A method for treating diabetic and non-diabetic chronic kidney disease, the method comprising administering to a patient in need thereof a of using a pharmaceutical composition comprising a pharmaceutically effective amount of a compound of formula (I)

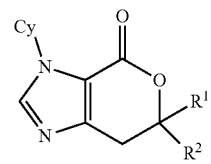

I or a pharmaceutically acceptable salt thereof, wherein:
Cy is a monocyclic or bicyclic ring system selected from $C_{3-10}$cycloalkyl, heterocyclyl, aryl and heteroaryl,
wherein each of the said $C_{3-10}$cycloalkyl, heterocyclyl, aryl and heteroaryl groups is optionally and independently substituted with one, two, or three substituent groups selected from halogen, —$C_{1-3}$-alkyl, —$OC_{1-3}$-alkyl, —$CF_3$, cyano, oxo, —$N(C_{1-3}$-alkyl)$_2$, —$NH(C_{1-3}$-alkyl), —$NHCOC_{1-3}$-alkyl, —$C(O)C_{1-3}$-alkyl, —$C(O)OC_{1-3}$alkyl, hydroxy-$C_{1-3}$alkyl, or heteroaryl; and
$R^1$ and $R^2$ are independently selected from H, $C_{1-3}$alkyl, hydroxy$C_{1-3}$alkyl, —$CH_2NHC(O)OC_{1-4}$alkyl, —$CH_2OC(O)C_{1-4}$alkyl, —$C(O)OC_{1-4}$-alkyl, —$C(O)H$, —$COOH$, —$C(O)NHC_{1-4}$-alkyl and $C(O)N(C_{1-4}$-alkyl)$_2$; or
$R^1$ and $R^2$ taken together form a $C_{3-6}$cycloalkyl or $C_{3-6}$-heterocyclyl, and a pharmaceutically acceptable excipient or carrier.

Embodiment 30: The method according to Embodiment 29, further comprising administering to the patient a pharmaceutically effective amount of a sodium-glucose cotransporter-2 (SGLT2) inhibitor, or a pharmaceutically acceptable salt thereof.

Embodiment 31: The method according to Embodiment 30, wherein the SGLT2 inhibitor is empagliflozin.

Embodiment 32: An aldosterone synthase inhibitor, or a pharmaceutically acceptable salt thereof, optionally in combination with a sodium-glucose cotransporter-2 (SGLT2) inhibitor, for use in the treatment of diabetic and non-diabetic chronic kidney disease, wherein the aldosterone synthase compound is of formula (I)

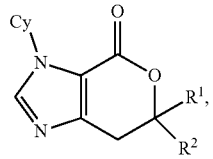

wherein:
Cy is a monocyclic or bicyclic ring system selected from $C_{3-10}$cycloalkyl, heterocyclyl, aryl and heteroaryl,
wherein each of the said $C_{3-10}$cycloalkyl, heterocyclyl, aryl and heteroaryl groups is optionally and independently substituted with one, two, or three substituent groups selected from halogen, —$C_{1-3}$-alkyl, —$OC_{1-3}$-alkyl, —$CF_3$, cyano, oxo, —$N(C_{1-3}$-alkyl)$_2$, —$NH(C_{1-3}$-alkyl), —$NHCOC_{1-3}$-alkyl, —$C(O)C_{1-3}$-alkyl, —$C(O)OC_{1-3}$alkyl, hydroxy-$C_{1-3}$alkyl, or heteroaryl; and
$R^1$ and $R^2$ are independently selected from H, $C_{1-3}$alkyl, hydroxy$C_1$-3alkyl, —$CH_2NHC(O)OC_{1-4}$alkyl, —$CH_2OC(O)C_{1-4}$alkyl, —$C(O)OC_{1-4}$-alkyl, —$C(O)H$, —COOH, —$C(O)NHC_{1-4}$-alkyl and $C(O)N(C_{1-4}$-alkyl)$_2$; or
$R^1$ and $R^2$ taken together form a $C_{3-6}$cycloalkyl or $C_{3-6}$-heterocyclyl.

What is claimed is:

1. A method for treating a patient with chronic kidney disease (CKD), the method comprising administering compound 29A to the patient

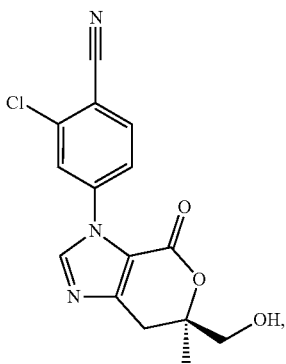

wherein compound 29A is administered once daily in an amount of 3 mg, 10 mg or 20 mg, and
wherein the treatment provides an improvement in albumin creatinine ratio (UACR) measured in First Morning Void (FMV) urine.

2. The method according to claim 1, wherein the patient has diabetic chronic kidney disease.

3. The method according to any of claim 1, wherein the patient has non-diabetic chronic kidney disease.

4. The method according to claim 1, wherein the patient has Stage 1 CKD, or Stage 2 CKD, or Stage 3 CKD, or Stage 4 CKD, or Stage 5 CKD.

5. The method according to claim 1, further comprising administering to the patient a pharmaceutically effective amount of a SGLT2 inhibitor, or a pharmaceutically acceptable salt thereof.

6. The method according to claim 5, wherein the SGLT2 inhibitor is empagliflozin.

7. The method of claim 1, wherein the patient has an estimated glomerular filtration rate (eGFR) ≥30 and <90 mL/min/1.73 m².

8. The method of claim 1, wherein compound 29A is administered to the patient in an amount of 10 mg.

9. The method of claim 6, wherein the empagliflozin is administered to the patient once daily in an amount of 10 mg.

10. A method for improving the albumin creatinine ratio (UACR) in a chronic kidney disease (CKD) patient, the method comprising administering to the patient compound 29A

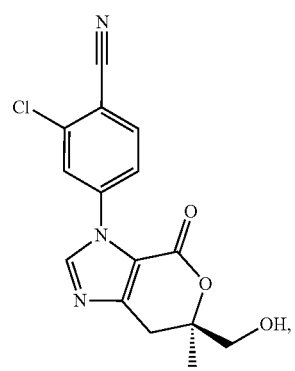

wherein compound 29A is administered once daily in an amount of 10 mg.

11. The method of claim 10, further comprising administering empagliflozin once daily to the patient.

12. The method of claim 11, wherein the empagliflozin is administered once daily to the patient in an amount of 10 mg.

13. The method of claim 10, wherein the patient has an estimated glomerular filtration rate (eGFR) ≥30 and <90 mL/min/1.73 m².

14. The method of claim 10, wherein the patient has diabetic chronic kidney disease.

15. The method of claim 10, wherein the patient has non-diabetic chronic kidney disease.

* * * * *